(12) United States Patent
MacAuslan

(10) Patent No.: US 9,526,458 B2
(45) Date of Patent: Dec. 27, 2016

(54) COUGH ANALYSIS

(71) Applicant: Speech Technology & Applied Research Corporation, Bedford, MA (US)

(72) Inventor: Joel MacAuslan, Nashua, NH (US)

(73) Assignee: Speech Technology and Applied Research Corporation, Bedford, MA (US)

( * ) Notice: Subject to any disclaimer, the term of this patent is extended or adjusted under 35 U.S.C. 154(b) by 0 days.

(21) Appl. No.: 14/255,436

(22) Filed: Apr. 17, 2014

(65) Prior Publication Data

US 2014/0343447 A1    Nov. 20, 2014

Related U.S. Application Data

(63) Continuation of application No. 12/886,363, filed on Sep. 20, 2010, now abandoned.

(60) Provisional application No. 61/252,581, filed on Oct. 16, 2009, provisional application No. 61/243,960, filed on Sep. 18, 2009.

(51) Int. Cl.
| | |
|---|---|
| *A61B 5/08* | (2006.01) |
| *A61B 5/00* | (2006.01) |
| *A61B 7/00* | (2006.01) |
| *A61B 7/04* | (2006.01) |

(52) U.S. Cl.
CPC ........... *A61B 5/7282* (2013.01); *A61B 5/0823* (2013.01); *A61B 7/003* (2013.01); *A61B 7/04* (2013.01)

(58) Field of Classification Search
CPC combination set(s) only.
See application file for complete search history.

(56) References Cited

U.S. PATENT DOCUMENTS

| | | | |
|---|---|---|---|
| 2006/0074334 A1* | 4/2006 | Coyle | 600/529 |
| 2007/0118054 A1* | 5/2007 | Pinhas et al. | 600/587 |
| 2010/0056951 A1* | 3/2010 | Banerjee et al. | 600/559 |
| 2012/0071777 A1* | 3/2012 | MacAuslan | 600/529 |

OTHER PUBLICATIONS

"System to Detect Severe Respiratory Illness by Vocalization Analysis of Cough", Sep. 28, 2008, 1 page. (Abstract NIH grant No. R43-HL096246).*
Thorpe, C. W., L. J. Toop, and K. P. Dawson. "Towards a quantitative description of asthmatic cough sounds." European Respiratory Journal 5.6 (1992): 685-692 (Thorpe).*

* cited by examiner

*Primary Examiner* — Michael Kahelin
*Assistant Examiner* — Mitchell E Alter
(74) *Attorney, Agent, or Firm* — Robert Plotkin, P.C.; Robert Plotkin, Esq.

(57) ABSTRACT

A computer-implemented method comprises: (A) receiving first acoustic data representing a first cough train of a first human subject, wherein the first cough train comprises at least one first cough of the first human subject; (B) identifying at least one first value of at one first acoustic property of the first acoustic data; and (C) determining, based on the at least one first value of the at least one first acoustic property, whether the first acoustic data indicates that the first human subject has a severe respiratory illness.

28 Claims, 9 Drawing Sheets

Cough Classifier Top-level Flowchart:
Classification Mode

FIG. 3: Cough Classifier Top-level Flowchart: Classification Mode

FIG. 4: Cough Database

FIG. 5: Cough Classifier Top-level Flowchart:
Training Mode

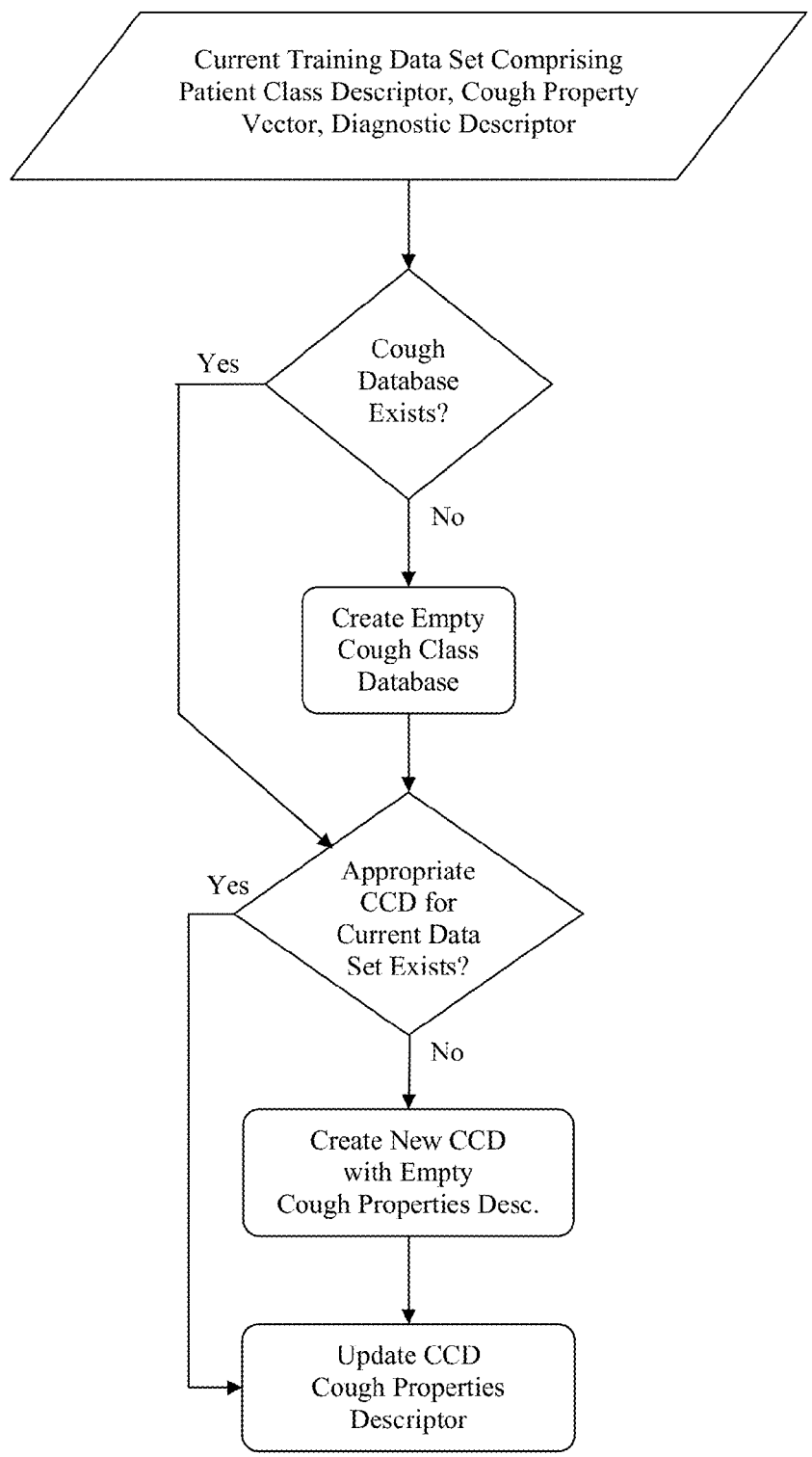
FIG. 7: Incremental Training of a Cough Class Descriptor

| Link to CCD1 | Candidate 1 Confidence Score |
|---|---|
| Link to CCD2 | Candidate 2 Confidence Score |
| ... | ... |
| Link to CCD N | Candidate N Confidence Score |

FIG. 8: Cough Class Candidate List

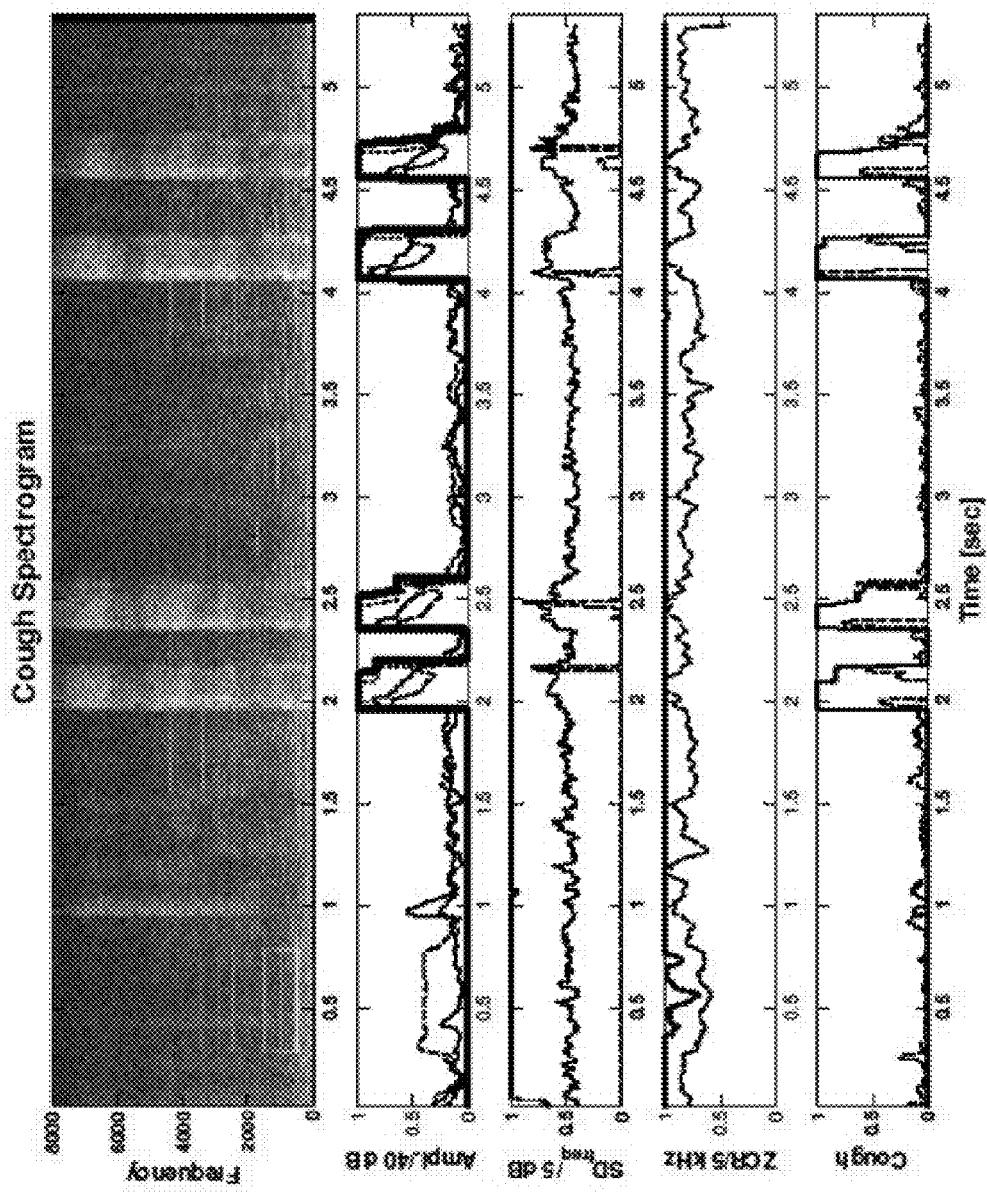
FIG. 9: Component Contours for Coughness and Flutter

COUGH ANALYSIS

STATEMENT AS TO FEDERALLY SPONSORED RESEARCH

This invention was made with Government support under NIH Grant #R43-HL096246, entitled, "System to Detect Severe Respiratory Illness by Vocalization Analysis of Cough." The Government has certain rights in the invention.

BACKGROUND

Cough is a mode of transmission of respiratory pathogens and a prominent symptom of severe cough-transmissible respiratory illness (SCTRI), such as influenza, tuberculosis (TB), and pertussis; as well as of other severe pathologies, especially pneumonia. Close contact between infected and uninfected groups, as among healthcare workers (HCWs) and patients can lead to rapid spread of SCTRI within and between the two groups, widespread illness, severe staffing shortages, and even deaths. Organisms are constantly being introduced from the community (by HCWs, visitors, and new patients) with potential transmission to those individuals who are most severely ill and, thus, most vulnerable to SCTRIs. Social isolation strategies used in epidemics are not well-suited for use in patient care. An important ongoing problem is that SCTRI is often not identified in patients or HCWs with cough early enough to prevent transmission to staff and other patients. Moreover, automatic assessment of cough as a vital sign would permit better clinical assessment of pneumonia, particularly in locations that are remote from clinical facilities.

The clinical interpretation of cough has always depended on individual judgment and the skill of the observer. Clinicians are taught to discern cough characteristics to distinguish infectious etiology and severity. Yet, it has been shown that such perception-based judgment has variable intra- and inter-rater reliability. In spite of these problems, the acoustic characteristics of cough have not previously been objectively quantified as the basis for a disease-screening tool or as a vital sign.

SUMMARY

One embodiment of the present invention is directed to a method comprising: (A) receiving first acoustic data representing a first cough train of a first human subject, wherein the first cough train comprises at least one first cough of the first human subject; (B) identifying at least one first value of at one first acoustic property of the first acoustic data; and (C) determining, based on the at least one first value of the at least one first acoustic property, whether the first acoustic data indicates that the first human subject has a severe respiratory illness.

Another embodiment of the present invention is directed to a method comprising: (A) receiving first acoustic data representing a first cough train of a first human subject, wherein the first cough train comprises at least one first cough of the first human subject; (B) identifying at least one first value of at least one first acoustic property of the first acoustic data; and (C) determining, based on the at least one first value of the at least one first acoustic property, whether the first acoustic data indicates that the first human subject has an abnormal pulmonary system.

Yet another embodiment of the present invention is directed to a method comprising: (A) requesting that a human subject cough; (B) using a microphone to receive live acoustic data representing a cough train of the human subject, wherein the cough train comprises at least one cough of the human subject; and (C) analyzing the live acoustic data to determine whether the cough train indicates that the human subject has a severe respiratory illness.

Other features and advantages of various aspects and embodiments of the present invention will become apparent from the following description and from the claims.

BRIEF DESCRIPTION OF THE DRAWINGS

FIG. 7 is a flowchart of a method for performing incremental training of a cough class descriptor according to one embodiment of the present invention;

FIG. 8 is a diagram of a cough class candidate list according to one embodiment of the present invention; and FIG. 9 are plots of component contours for coughness and flutter according to one embodiment of the present invention.

DETAILED DESCRIPTION

Figure 1:
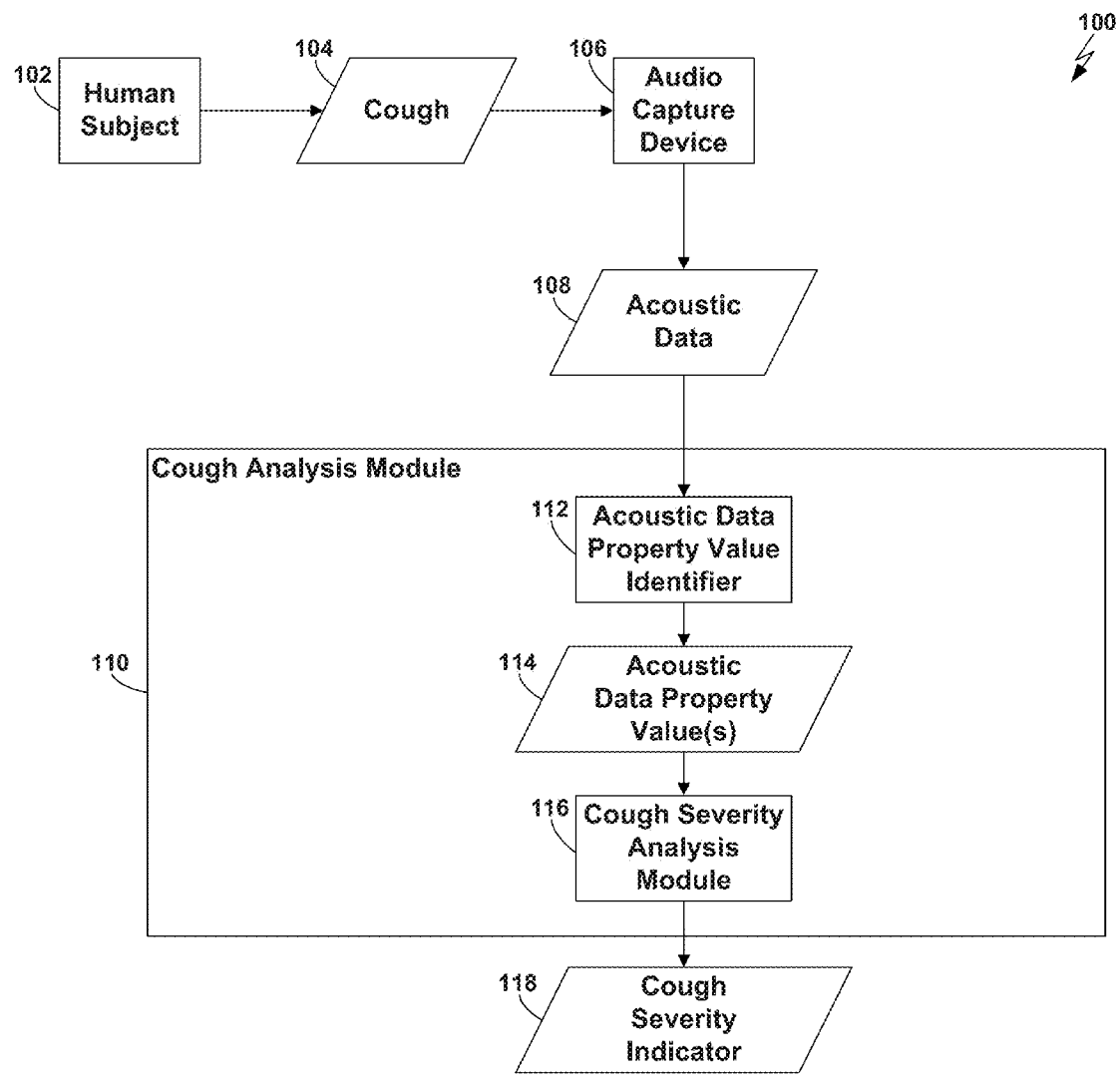
FIG. 1 is a dataflow diagram of a system for analyzing a cough according to one embodiment of the present invention.
Figure 2:
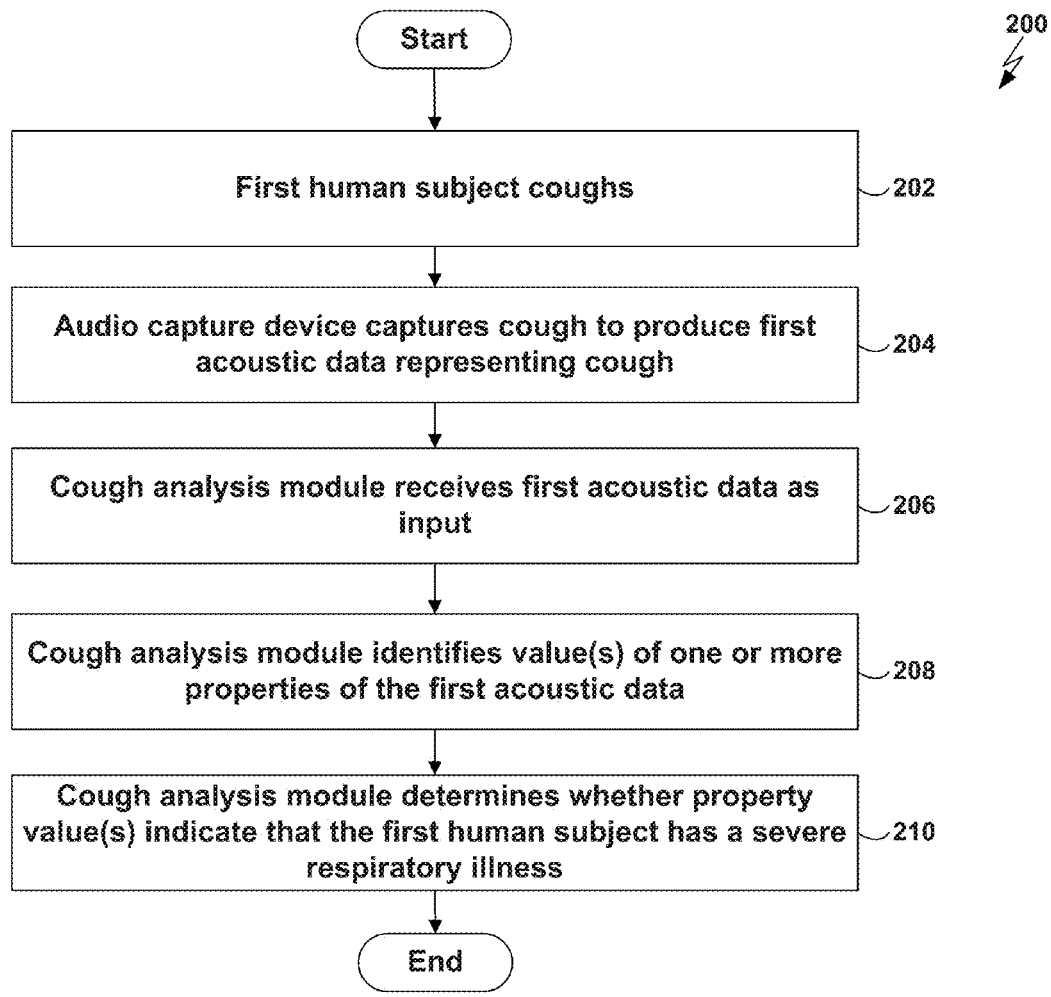
FIG. 2 is a flowchart of a method performed by the system of FIG. 1 according to one embodiment of the present invention.

Referring to FIG. 1, a dataflow diagram is shown of a system 100 for analyzing a cough according to one embodiment of the present invention. Referring to FIG. 2, a flowchart is shown of a method 200 performed by the system 100 of FIG. 1 according to one embodiment of the present invention.

As shown in FIG. 1, a first human subject 102 coughs, thereby producing sound waves 104 (FIG. 2, step 202), which are captured by an audio capture device 106, thereby producing as output first acoustic data 108 representing the cough 104 (FIG. 2, step 204). The audio capture device 106 may be any kind of acoustic data acquisition device, such as a standalone microphone not in contact with the body of the first human subject 102. The human subject 102 may, for example, produce the cough 104 spontaneously, or in response to a request that the human subject 102 cough.

The first acoustic data 108 may be live (e.g., provided as output by the audio capture device 106 immediately or shortly after being produced by the audio capture device 106), or recorded and produced as output by the audio capture device 106 after an appreciable delay (e.g., a few minutes or hours after production of the cough 104).

A cough analysis module 110 receives the first acoustic data 108 as input (FIG. 2), step 206). The first acoustic data 108 may have one or more acoustic properties, each of which may have its own particular value within a range of possible values for that property. An acoustic data property value identifier 112 in the cough analysis module 110 identifies the value(s) 114 of one or more predetermined acoustic properties of the first acoustic data 108 (FIG. 2, step 208).

A cough severity analysis module 116 within the cough analysis module 110 determines, based on the acoustic data property values 114, whether the first acoustic data 108 indicates that the first human subject 102 has a severe respiratory illness (such as a severe cough-transmissible respiratory illness (SCTRI) or a severe cough-generating respiratory illness (SCGRI)) (FIG. 2, step 210). Examples of SCTRIs are tuberculosis, influenza (flu), pertussis, and pneumonic plague. Examples of SCGRIs are non-transmissible pneumonias and other severe illnesses that generate coughs. A SCGRI may or may not be a SCTRI. The cough severity analysis module 116 provides as output a cough severity indicator 118 which indicates the cough analysis module's determination of whether the first human subject 102 has a severe respiratory illness.

Alternatively, for example, the cough severity analysis module 116 within the cough analysis module 110 may determine, based on the acoustic data property values 114, whether the first acoustic data 108 indicates that the first human subject 102 has a non-severe respiratory illness, or that the first acoustic data 108 indicates that the first human subject 102 does not have a severe respiratory illness.

As yet another alternative, in step 210 the cough severity analysis module 116 may determine, based on the acoustic data property values 114, whether the first human subject 102 has a normal (also referred to as "ordered" or "healthy") pulmonary system, or whether the first human subject 102 has an abnormal (also referred to as "disordered" or "diseased") pulmonary system.

If the cough severity analysis module 116 determines that the first human subject 102 has an abnormal pulmonary system, the cough severity analysis module 116 may further determine, based on the acoustic data property values 114, whether the first acoustic data 108 indicates that the first human subject 102 has a severe (cough-transmissible) respiratory illness, whether the first acoustic data 108 indicates that the first human subject 102 has a non-severe respiratory illness, or that the first acoustic data 108 indicates that the first human subject 102 does not have a severe respiratory illness.

Similarly, if the cough severity analysis module determines that the first human subject 102 has an abnormal pulmonary system, the cough severity analysis module 116 may further determine, based on the acoustic data property values 114, whether the first acoustic data 108 indicates that the first human subject 102 has a severe respiratory illness, or whether the first acoustic data 108 indicates that the first human subject 102 has a non-severe respiratory illness, or that the first acoustic data 108 indicates that the first human subject 102 does not have a severe respiratory illness.

The cough analysis module 110 may perform any of the analyses described above and produce the cough severity indicator 118 immediately after, and in response to, receiving the first acoustic data 108 from the audio capture device 106, or after an appreciable delay (e.g., a few minutes or hours after production of the cough 104) after receiving the first acoustic data 108 from the audio capture device 106.

The method of FIG. 2 may be repeated for people other than the first human subject 102. For example, a second human subject (not shown) may cough, thereby producing second sound waves, which may be captured by the audio capture device 106, thereby producing as output second acoustic data representing the second cough, in the manner described above.

The cough analysis module 110 may receive the second acoustic data and identify one or more second values of the one or more predetermined acoustic properties, in the manner described above. The cough severity analysis module 116 may determine, based on the second acoustic data property values, whether the second acoustic data indicates that the second human subject has a severe respiratory illness, in the manner described above. The cough analysis module 110 may, for example, determine that the first human subject 102 has a severe respiratory illness and that the second human subject does not have a severe respiratory illness, that both the first and second human subjects have severe respiratory illnesses, or that neither the first human subject 102 nor the second human subject has a severe respiratory illness. The cough analysis module 110 may further process the second acoustic data in any of the additional or alternative ways described above with respect to the first acoustic data 108.

Similarly, the second cough may be obtained from the first human subject 102, at a second time than the first cough 104, instead of from a second human subject. Any of the processing described above with respect to the second cough of the second human subject may be applied to the second cough of the first human subject.

In the examples provided above, the cough 104 is described as a single cough. However, alternatively the cough 104 may be a plurality of coughs of the human subject 102, referred to herein as a "cough train." The same or similar techniques as those described above may be applied to such a cough train.

It has been assumed in the examples described above that the sound 104 is a cough. The cough analysis module 110 may assume that the sound 104 produced by the first human subject 102 (and other sounds produced by the same or other human subjects) is a cough. Alternatively, for example, the cough analysis module 110 may not assume that the sound 104 is a cough, but instead analyze the first acoustic data 108 to determine whether the sound 104 is a cough. In particular, the cough analysis module 110 may determine, based on one or more values of one or more second acoustic properties (which may be the same as or different from the first acoustic properties), whether the first acoustic data 108 represents a cough. The cough analysis module 110 may then only proceed to make other determinations described above (such as whether the first human subject 102 has a severe respiratory illness, or whether the first human subject has an abnormal pulmonary system) if the cough analysis module 110 first determines that the first acoustic data 108 represents a cough.

The system 100 may, for example, determine that the sound 104 produced by the first human subject 102 is a cough, but that a sound (not shown) produced by a second human subject is not a cough, or that a sound was not produced by a human subject and therefore is not considered to be a cough.

As mentioned above, the cough severity analysis module 116 may determine that the first acoustic data 108 indicates that the first human subject 102 has a severe cough-transmissible respiratory illness. In this case, the cough severity analysis module 116 may further identify, based on the acoustic data property values 114, a type of the severe cough-transmissible respiratory illness. As part of or in addition to this determination, the cough severity analysis module 116 may determine whether the severe cough-transmissible respiratory illness is of a type that can propagate via epidemics.

The set of one or more acoustic properties whose values are identified in step 112 may be selected in any of a variety of ways. For example, one or more of the acoustic properties whose values are identified in step 112 may be an instance of a landmark marking a point in the first acoustic data 108 that marks a discrete event. Such landmark instances may, for example, be instances of consonantal landmarks and/or instances of vocalic landmarks. Landmark instances may be used, for example, to identify one or more of the inspiration phase of the cough 104, the compression phase of the cough 104, and the expiration phase of the cough. Any particular landmark instance is an instance of a corresponding landmark, as defined by a landmark definition. Different landmark instances may be instances of different landmarks defined by different landmark instances.

Cough Classification Algorithm

The Cough Classification Algorithm (the "Cough Classifier") described below processes an audio recording of a stream of Acoustic Data 108 from a Human Subject 102 who possibly produced one or more Coughs 104 into an Audio Capture Device 106 to 1) extract a "Coughness" contour that identifies cough-like regions in the recording; 2) extract other contours of local and cumulative properties that are relevant for classifying different types of cough based on the acoustic (audio) data in the recording; 3) generate a single vector of Acoustic Data Property Values 114 from the extracted contours; 4) compare the generated properties vector with comparable information in a database of known types, or classes, of coughs; 5) construct a list of coughs in the database that are similar to the coughs in the utterance; 6) classify the coughs (if any) in the recording either as dissimilar to all known coughs in the database, or as substantially similar to a plurality of known coughs in the database; and 7) based on that classification, determine a possible patient diagnosis or other Cough Severity Indicator 118 associated with the plurality of similar known coughs, and therefore the likelihood that the human subject has a severe respiratory illness (Step 210 in FIG. 2).

The audio recording is assumed to be the utterance of a single patient, and may contain an arbitrary number of coughs (zero, one, or more than one). Significantly, if there is more than one cough in the recording, some or all of the coughs may be organized into one or more "trains" of contiguous coughs.

In addition to the audio recording, an additional input to the algorithm is Patient Information that contains demographic and health-related information about the patient, such as the patient's age, sex, and smoking history. The Cough Classifier also makes use of training data, in the form of a Cough Class Database (the "Cough DB"). The Cough DB comprises a plurality of Cough Class Descriptors ("CCDs"). Each CCD describes a particular Cough Class.

Each CCD comprises a patient class descriptor, a cough properties descriptor, and a diagnostic descriptor. The Cough DB is populated with CCDs by the Cough DB Training Process, described below. By examining CCDs that have patient class descriptors compatible with the current Patient Information to find those CCDs that have cough descriptors similar to the coughs in the utterance, a list of diagnostic descriptors can be found that constitute diagnostic predictions for the patient that generated the cough.

The output of the Cough Classifier is a pair of values which identifies a single Cough Class Descriptor, and indicates the likelihood that the processed utterance comprises one or more coughs of the type described by the identified Cough Class Descriptor. A null output value is generated when the Cough Classifier does not find any known Cough Class in the utterance being processed.

Alternatively, the Cough Classifier can output a Cough Candidate List. This List is a list of Cough Class Descriptor/Likelihood pairs. Each pair represents a unique Cough Class Descriptor from the Cough DB. The corresponding likelihood value represents the likelihood that the recorded utterance comprises coughs of the specified type or class.

The Cough Classifier runs in two modes: Training Mode and Classification Mode. In Training Mode, it processes a plurality of cough recordings, each with accompanying Patient Information and Diagnostic Information. A collection of such triples (utterance, patient info, and diagnostic info) are used to "train" the Cough Class Database: that is, to populate the Database with appropriate Cough Class Descriptors.

Figure 3:
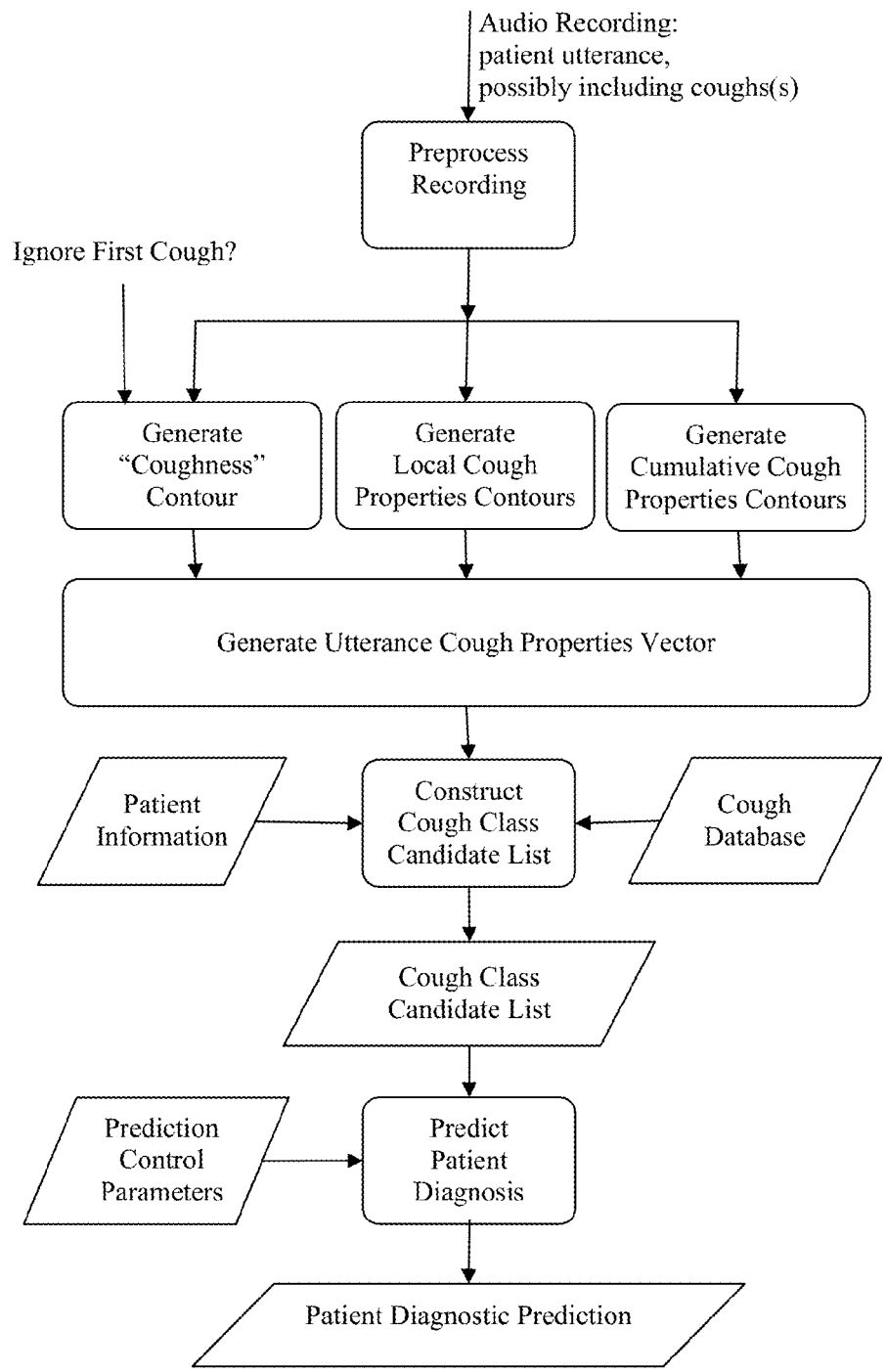
FIG. 3 is a flowchart of a method performed by a cough classifier in classification mode according to one embodiment of the present invention.

In Classification Mode, the Cough Classifier analyzes a recording which typically comprises one or more coughs by a new patient, and uses accompanying Patient Information to select one or more comparable CCDs in the Cough DB. The Cough Classifier may further analyze these "candidate" CCDs to generate a diagnostic prediction for the new patient using the diagnostic descriptors found in the selected CCDs. Thus in Classification Mode, the Cough Classifier shown in FIG. 3 constitutes an implementation of Cough Analysis Module 110. The Audio Recording input to the Cough Classifier constitutes Acoustic Data 108. The steps shown in FIG. 3 and described below of preprocessing the Recording, generating the Coughness, Local Cough Property, and Cumulative Cough Property Contours, and Generating the Utterance Cough Properties Vector constitute an implementation of Acoustic Data Property Value Identifier 112. A Cough Properties Vector is an Acoustic Data Property Value 114. The steps shown in FIG. 3. and described below of constructing a Cough Class Candidate List, and predicting a Patient Diagnosis constitute an implementation of Cough Severity Analysis Module 116, and the Patient Diagnostic Prediction output of the Cough Classifier operating in Classification Mode, shown in FIG. 3 and described below, is an implementation of Cough Severity Indicator 118.

Preprocessing the Recording

The audio recording is preprocessed using techniques well-known to persons of ordinary skill in the art to normalize for sampling rate, bit depth, and amplitude range. Preferably the result of this preprocessing is a single-channel uncompressed signal with an effective sampling rate of 16 KHz, samples represented as signed 16-bit binary numbers, and a typical signal amplitude, in those portions of the utterance where a cough is present, greater than or equal to −40 dB. Preferably the preprocessing method will detect and flag utterances that are too quiet and utterances that were too loud and therefore exhibit "clipping".

Generating the Coughness Contour

The Coughness and Property Contours are time series of calculated values, each value of which represents a particular property of the preprocessed audio recording at a given point in time. Usefully the contours may be down sampled from the audio sampling rate. One thousand contour values per second is a useful rate. Thus, a contour value with an index of 1500 would represent a property of the audio recording 1.5 seconds after the beginning of the recording. Even further down-sampling may be performed if desired.

As values of contours are calculated, previously calculated contour values for the same utterance may usefully be employed in calculating additional contour values.

The Coughness Contour value corresponding to a particular time in the recording specifies how "cough-like" the recorded audio is at that moment in time. A Coughness value of 0.0 indicates that the recorded audio at the corresponding time is not at all cough-like. A Coughness value of 1.0 indicates that the recorded audio at the corresponding time is completely cough-like.

In one possible implementation, Coughness values for a 16-kHz signal are calculated in the following manner. These will be demonstrated in FIG. 9 on a recording of two pairs of coughs; this recording also contains background sounds consisting of non-cough impulses, human speech, and pure tones from equipment in the health-care environmental.

The following description uses the following notation:
CL(x,a,b)=max(0, min(1, (x−a)/(b−a))), i.e., linear scaling and clipping to the range 0 to 1.
Result=the name associated with an immediately preceding computation; for example, y=(2*3)+5 may be described as "Multiply 2 by 3; then y=Result+5".

In what follows, we make frequent use of so-called morphological (or rank-filter) operations, particularly:
the median filter, which replaces the value at each position in a signal with the median of the values in a specified neighborhood about the position;
Dilation, or max-filter, similarly;
Erosion or min-filter, similarly;
Opening, or Erosion followed by Dilation over the same neighborhood; and
Closure, or Dilation followed by Erosion, similarly.
All of these functions have standard implementations in the MATLAB® Signal and Image Processing Toolboxes (as MEDFILT1, IMDILATE, IMERODE, IMOPEN, and IMCLOSE, respectively). In all cases, unless stated otherwise, these filters will be applied to symmetrical neighborhoods, i.e., using one-half of the specified time interval or number of samples on either side.

We also use the conventional fuzzy-logic operators And(.,.) and Or(.,.), equivalent to min(.,.) and max(.,.) for the contour arrays used here. These will be used exclusively on arrays taking values between 0 and 1 (typically the results of CL).

Coughs are characterized by acoustic properties that may be summarized by several rules, which will guide the implementation below. In most cases, coughs follow all of these rules and may be located in the audio stream (acoustic signal) by the conjunction of the rules; in a few cases, however, the rules express alternatives, which will be pointed out when they arise. These rules may be expressed in a variety of forms or embodiments; we will express them here in a form that is generally amenable to direct implementation in MATLAB or other high-level programming languages, particularly in terms of morphological operations and fuzzy logic. The first group of these concern its amplitude:

The peak amplitude of any cough is no more than 20 dB fainter than the signal's global peak amplitude.
The smallest amplitude within a cough is no more than 20 dB fainter than the peak within that cough.
The cough duration is typically C=500 ms long, and always at least D=120 ms.
Each cough is separated from any adjacent coughs by at least I=50 ms.
The onset of each cough includes a rise of at least 15 dB in at most R=12 ms.
The onset of each cough to its maximum is at least T=15 ms.

Other rules concern its spectrogram's temporal and, especially, spectral structure:
All broad frequency ranges within 1-7 kHz rise and fall together.
The mouth retains a relatively fixed shape throughout the cough. Thus, at each time (spectrogram frame), the difference between the maximum over frequency and the median over frequency lies in the range 30-45 dB. Conversely, this difference typically lies in the range 5-20 dB outside of coughs.
Unlike non-mouth sounds, frequency structure arises from the formants, i.e., resonances of the mouth. Thus, at each time, the standard deviation over frequency is at least 3.5 dB, typically at least 4.0 dB, especially if the onset has occurred at least 100 ms previously.

In addition, coughs are characterized by one-half of zero-crossing rates (i.e., ZCR/2) of at least 2 kHz and typically 3.5 kHz or more, for at least U=20 ms. The zero-crossing rate is simply the rate at which the signal changes sign, averaged over a suitable interval such as 20 ms.

As we shall see, the morphological operations are used for enforcing the various duration constraints. In addition, median-filtering suppresses extremes without substantially changing either intermediate values or contour shapes.

1. We begin by computing the spectrogram of the signal, using the standard MATLAB® function call:
20*LOG 10(ABS(SPECGRAM(signal, 512, 16000, 256, 1))),
which produces 32-Hz resolution and a 16-kHz sampling rate. (Conventionally, this is shown as an image with frequency as the vertical axis and time as the horizontal, as displayed at the top of FIG. 9. The signal amplitude, i.e., square root of energy integrated across frequencies, is shown in dB, divided by 40 dB, as the dashed contour in the second panel of FIG. 9.) Realistically, a sampling rate of 256 Hz is sufficient; however, the present form provides contours that have exactly the sampling rate of the underlying signal, an expository convenience. Another embodiment would replace the final argument, unity, with 16, for 1-kHz sampling (16-fold down-sampling); 64, for 256-Hz sampling (64-fold down-sampling); or the like.

Then let S be the median filter of this spectrogram over 5 adjacent frequency bands (i.e., "vertically" in the spectrogram); the median-filtering suppresses sustained pure tones; the effect of this may be seen in the second panel of FIG. 9, wherein the square root of energy integrated across frequencies of this median-filtered spectrogram is shown in dB, divided by 40 dB, as the light solid contour; it will be seen that the energy in the pure tones, e.g., at 0.3-0.8 s, has been removed compared to the amplitude from the unfiltered spectrogram. Let S1 be S restricted to the frequency range 100-1000 Hz, and S7 be S restricted to 1000-7000 Hz. These spectrograms are thus all measured in dB.

2. Next, smooth S7 over frequencies with a 2-kHz-wide ("vertical") window using a unit-integral convolution, using the MATLAB® function call:
CONV2 (S7, ONES(N, 1)/N, 'same'),
where N=64, the number of frequency bands in 2 kHz. (The kernel has unit integral because SUM(ONES(N, 1)/N)=unity.) Then compute the standard deviation (over all frequencies) of this. Note that this is a contour, i.e., function only of time. Let
σ=median-filter(Result) over 15 ms.
This, divided by 5 dB, is shown as the irregular solid contour in the $3^{rd}$ panel of FIG. 9. It will be seen that σ rises significantly above its typical value (about 2.5 dB, i.e., one-half of full-scale in the figure) only within the four coughs.

3. We also compute Z=one-half of the zero-crossing rate of the signal over 60-ms windows (a contour that takes on the values 0-8000 Hz). Let z5, z20, z90 and z98 be the 5th, 20th, 90th and 98th percentiles, respectively, of the Z values so computed. Then let DegZ0=CL(Z, 2000 Hz, 3500 Hz), Opened over U=20 ms; and
DegZ=DegZ0, Dilated over I=50 ms;
DegZlower=CL(Z, z5, z20);
DegZupper=CL(Z, z98, z90), various contours of the degree to which the signal is cough-like based on its ZCR. Notice that DegZupper enforces a rule that extremely high values of Z are not cough-like. The contour of Z itself, divided by 5000 Hz (its maximum value in this recording), is shown as the dashed contour in the 4th panel of FIG. 9; and DegZ is shown as the solid contour in the same panel. Notice that DegZ is lower than unity only where Z is lower than 3500 Hz (70% of full scale in the plot), and, by virtue of the Dilation, only near 0.6 s, where this lower value is sustained over I=50 ms.

4. Determine the mean of S7 over frequencies; this may be considered the envelope or amplitude of the band-pass filtered version of the signal (with band-pass 1-7 kHz). Note that this is a contour. Clip this at 40 dB below its maximum, and median-filter this over 22 ms to define M7. (As described earlier, this is represented as the light, solid contour in FIG. 9's second panel.) Let M1 be the similarly computed median-filtered, clipped mean of S1, and define a binary contour mask K as unity at the times when M1 and M7 are both positive, and zero otherwise.

Next, determine two thresholds as the 20th and 30th percentiles of the K-masked parts of M7 (thus excluding all zero values in M7, at least), and let X7=max(M7). These will be used shortly.

5. Let Low1=max(M1)−25 dB, and Med1=median(M1 where K>0), and then evaluate
s=CL(M1, Low1, Med1), dilated by 15 ms, and
DegMP=And(s, CL(M7, X7-25 dB, X7-15 dB)).

6. Dilate M7 by C=500 ms, and subtract M7 itself from this. Determine the $89^{th}$ and $92^{nd}$ percentiles of this contour, t89 and t92 respectively. Let
u=CL(Result, t89, t92).
Then dilate DegMP by D+I/2=145 ms, and combine this with u and M7, thus:
DegMA=And(Result, u, CL(X7-M7, X7-θ, X7-φ)),
the contour of degrees to which the signal is cough-like based on the spectrogram Mean's Amplitude. DegMA is shown in FIG. 9's second panel as the dotted contour. (This is most visible at the trailing edges of the four coughs; it is either zero or unity nearly everywhere else.)

7. Compute CL(DegMA, 0, ½), and define
DegMT=And(Closure of Result over I=50 ms,
Opening of Result over D=120 ms),
the contour of degrees to which the signal is cough-like based on the spectrogram Mean's Timing, i.e., durations of the cough, at least 120 ms, and of inter-cough gaps, at least 50 ms.

8. Next, median-filter over 30 ms, and let
DegFV=CL(Result, 3.5 dB, 4.0 dB),
the contour of degrees to which the signal is cough-like based on the spectrogram's Frequency Variation. This is shown as the dotted contour in FIG. 9's $3^{rd}$ panel.

9. Find the first difference of the contour M7 across R=12 ms in time. Then clip and scale this result:
w=CL(Result, 5 dB, 15 dB); and
DegMO1=Dilation of w backward over T+I=65 ms,
where the backward dilation applies the dilation to previous times. This is equivalent to computing, about each sample, the maximum over a neighborhood extending from the present sample to samples up to 65 ms later in time, i.e., covering any interval shorter than the inter-cough gap (>50 ms) plus the onset time (>15 ms).

10. Dilate M7 forward over T=15 ms, and subtract M7 itself from this. Then define
DegMO2=CL(Result, 30 dB, 20 dB), and
DefMO=And (DegMO1, DefMO2),
the contour of degrees to which the signal is cough-like based on the spectrogram Mean's Onset.

11. Dilate DegMA backward by 50 ms, and let Mmask=And(Result, DegMT dilated by 30 ms).
Next, dilate DegMO backward by 100 ms, and compute:
g=And(Result, Mmask), and
DegM=And(Dilation of g backward by 300 ms, Mmask).
DegM is a contour for the degrees to which the signal is cough-like based on the spectrogram's Mean values (across frequency). It is shown as the heavy solid contour in the second panel; notice that it is zero except at or near the coughs, and unity at most times in the coughs.

12. Find max(S7)−median(S7) over frequencies, i.e., at each time (each frame), and let
h=median-filter Result over 15 ms;
DegF1=CL(h, 30 dB, 25 dB),
DegF2=CL(Dilation of h backward over I+100 ms=150 ms, 5 dB, 10 dB),
DegFT=And(DegF1, DegF2),
i.e., the contour of degrees to which the signal is cough-like based on the Timing of the spectrogram's Frequency structure. This appears in the 3rd panel as the solid contour that is unity nearly everywhere, after a few initial values of 0.6 or more.

13. Dilate the contour And(DegFT, DegMA), backward by I+100 ms=150 ms, and let
DegF=Or(DegFT, And(Result, DegFV)),
i.e., the contour of degrees to which the signal is cough-like based on its spectrogram's Frequency structure. The fuzzy Or appears because coughs may have high degree if the timing of the frequency structure (DegFT) is high or, alternatively, if the specified contour using DegFV, DegFT, and DegMA is high. In FIG. 9, this is coincident with DegFT in the 3rd panel, because DegFT is unity (the maximum possible fuzzy value) throughout most of the recording.

14. Finally, combine these degrees:
q=And(DegM, Or(DegF, DegZ)),
r=And(DegMA, DegZlower, Or(q, DegZupper)),
DegCough=Opening of r by D=120 ms,
so that DegCough, or Coughness, may be considered the contour of degrees to which the signal is cough-like based on the various criteria derived from its spectrogram and ZCR. Again, the use (twice) of fuzzy Or occurs because some aspects of coughs may be characterized by alternative contours, such as the choice of either DegF or DegZ in the definition of q. Coughness is shown as the solid contour in the bottom panel of FIG. 9; for this recording, it is very similar to DegM, the heavy contour of the second panel.

The interpretation of this expression for Coughness may be phrased thus: The signal is cough-like to the degree that r is cough-like throughout a duration of at least D; and r itself is cough-like to the degree that:

M7's amplitude is cough-like (via DegMA) and

Z is minimally cough-like (via DegZlower) and either Z (via DegZupper) or q is cough-like.

Finally, q is cough-like to the degree that:

M7 is, overall, cough-like (via DegM) and either Z is cough-like (via DegZ) or the frequency structure is cough-like (via DegF).

This completes the description of the present embodiment of the computation of the Coughness values.

Generating the Local Cough Property Contours

A plurality of Local Cough Property Contours are calculated from the preprocessed audio recording, and, optionally, previously-calculated Contour values for the current utterance. Each Contour represents some value of the recorded utterance in a short period of time (usually in the range of 30 to 100 msecs) centered on the point in the recording corresponding to the index of the contour value. Typical contours correspond to local acoustic properties of the recording. If a cough is present at a given time in a recording, the values of the local contour values corresponding to that time will correspond to acoustic properties of the recorded cough.

Flutter, or local envelope standard deviation, is one of the Local Cough Properties that is extracted. It is computed as follows (with notation similar to the above):

1. Compute the local envelope E with the MATLAB® function call:

E0=SQRT(CONV2(ABS(signal).^2, ONES(1, K)/K, 'same')), where K is the number of samples to cover 25 ms (400 samples at 16 kHz).

2. Reduce all rapid fluctuations in E0, corresponding to 64-sample (4-ms) averaging, to define:

E=CONV2 (E0, ONES (1, 64)/64, 'same').

3. Remove the overall envelope contour, whose variations are large, by subtracting a median-filtered version of E, to define:

F=E−median-filter(E over 30 ms).

4. Compute the local standard deviation (i.e., contour), using the MATLAB® function STDFILT over 30 ms:

Flutter=STDFILT(F, N), where N is the number of samples in 30 ms (480 samples at 16 kHz). Flutter (divided by its maximum value, approximately 2.9e-4) is shown as the dotted contour in the bottom panel of FIG. 9. For this recording, the mean value of Flutter, weighted by Coughness, is 5.4e-5.

Another measure is the number of coughs recorded. This is most easily computed simply by thresholding the Coughness contour itself at a value such as and labeling the connected regions that exceed this threshold, using the MATLAB® function BWLABEL:

R=BWLABEL(REPMAT(DegCough>½, [3, 1])).

(The use of REPMAT creates three identical copies of the labeling "contour", because of limitations of BWLABEL. The first row, R(1,:), may be extracted for convenience.) Because the regions are denoted by consecutive positive Integers, the number of coughs (four, in the example recording) is just given by its maximum:

Ncoughs=MAX(R(1,:)), and the contour of the number of coughs identified up to a given time ("Cough Number Contour", as in FIG. 6) may be calculated with the MATLAB® expression such as CoughNumber=CUMSUM(MAX(0, DIFF(MAX(R (1,:))))).

Generating the Cumulative Cough Property Contours

A plurality of Cumulative Cough Property Contours is calculated from the preprocessed audio recording, and, optionally, previously-calculated Contour values for the current utterance. Each Cumulative Contour value represents some cumulative property of the region of the current utterance from its beginning to the point in time corresponding to the index of the Contour value.

Figure 6:
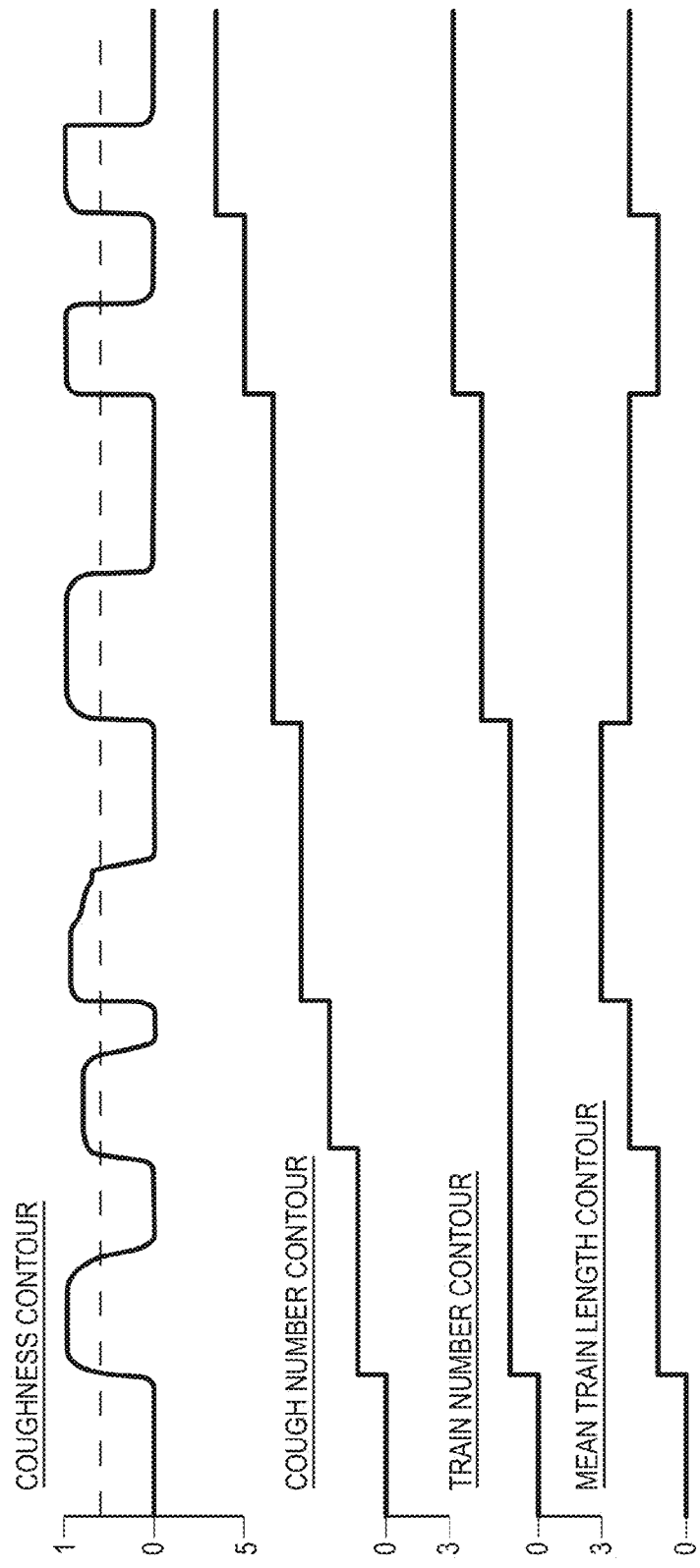
FIG. 6 is a set of plots of cumulative cough properties contours according to one embodiment of the present invention.

FIG. 6 shows an example Coughness Contour, and three corresponding Cumulative Cough Property Contours. The first property, "Cough Number", indicates the number of coughs that have been detected at any point in an utterance—from the beginning of the utterance to the point in time corresponding to the index of the contour value. (Calculation of this is described in the previous section.) The value of the Cough Number property is always zero at the beginning of an utterance, and increases by one each time a new cough is detected. (In FIG. 6, a new cough is considered to have been detected each time the Coughness Contour value exceeds a certain threshold, such as ½, indicated by the dashed line in FIG. 6.

The second cumulative property, "Train Number", indicates the number of cough trains that have been detected at any point in an utterance. A cough train is a single isolated cough, or a plurality of sequentially contiguous coughs. Two coughs are contiguous only if they are separated from each other by less than 1.4 seconds, and are not separated by an inhalation of 400 msecs or more. The value of the Train Number property is always zero at the beginning of an utterance, and increases by one each time a new cough train is detected.

The third cumulative property, "Mean Train Length Contour", indicates the mean (average) number of coughs in a train at any point in an utterance. The value of this property at any time index is calculated as the Cough Number property at the same index, divided by the value of the Train Number property, also at the same index.

Generating the Cough Property Vector

A single vector of Cough Properties is calculated for each utterance. This vector summarizes the extracted properties of the detected coughs in the current utterance. One useful way to calculate the elements of this vector is as follows:

For each Local Cough Property Contour, the inner product of that Contour and the Coughness Contour is calculated. That is, the sum of the product of the Coughness and Property values at corresponding times is calculated. Each such inner product becomes an element in the Cough Properties Vector. The weighted mean flutter, described earlier, is such an inner product (apart from dividing by the mean value of Coughness).

For each Cumulative Cough Property Contour, the final value of the Contour becomes another element in the Cough Properties Vector.

The Cough Properties Descriptor

In Training Mode, the Cough Classifier creates a Cough Properties Descriptor that characterizes and summarizes the expected range of values of Cough Property Vectors for patients in a single Patient Class and with similar Diagnostic Descriptors. In one implementation, the Cough Properties Descriptor is a list of all of the Cough Property Vectors of all of the training data for that Class. In an alternative implementation, the Cough Properties Descriptor is the multi-dimensional Gaussian random variable that best fits the set of all of the Cough Property Vectors in the training data for that Class, represented by specifying the mean and standard deviation vectors that define that Gaussian random variable.

The actual Cough Properties Descriptor may be constructed as a binary structure, an SQL record, an XML document, or many other formats that will occur to person of ordinary skill in the art.

Training the Cough DataBase (Training Mode)

Figure 4:
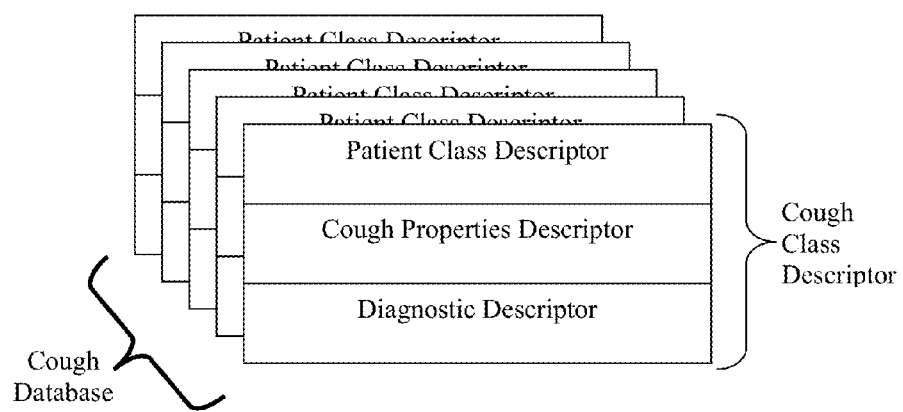
FIG. 4 is a diagram of a cough database according to one embodiment of the present invention.

As indicated by FIG. 4, a Cough Class Descriptor comprises a Patient Class Descriptor, a Cough Properties Descriptor, and a Diagnostic Descriptor. Each CCD in a Cough Database is created by the operation of the Cough Classification Algorithm in Training Mode. As shown in FIG. 7, the Cough Algorithm trains the Cough Database by incrementally creating and updating the CCDs in the Cough Database using the plurality of cough recordings available to it in Training Mode.

Figure 5:
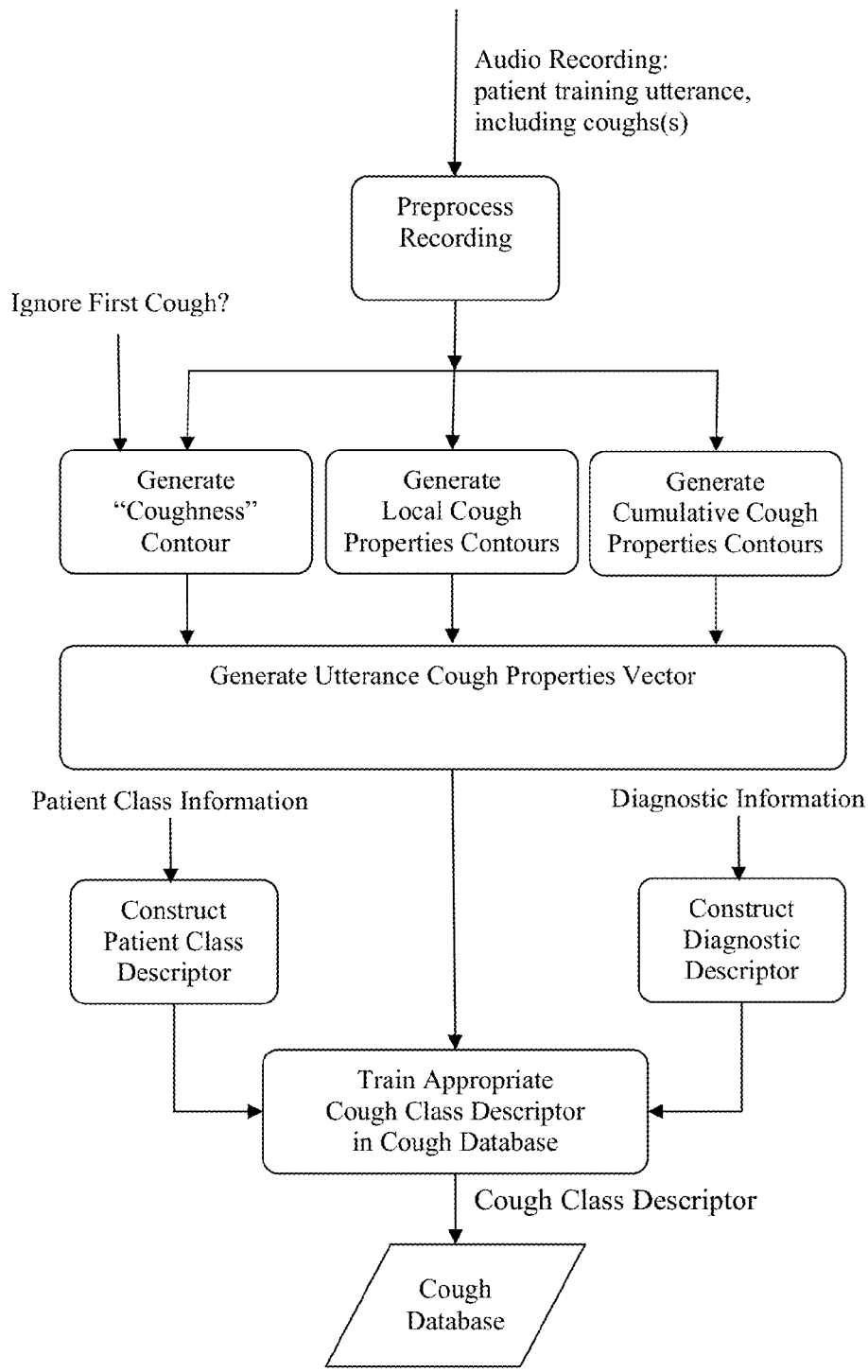
FIG. 5 is a flowchart of a method performed by a cough classifier in training mode according to one embodiment of the present invention.

In one implementation, the Cough Database is trained by processing each cough recording and other information in the training data set as shown in FIG. 5.

For each available training set of recorded coughs, Patient Class Information, and Diagnostic Information, the Cough Algorithm generates a Coughness Contour and Local and Cumulative Cough Property Contours. In one implementation, an optional configuration flag may specify that the first cough of every recording is to be ignored. This configuration flag may be useful if the procedure for collecting the cough recordings is such that the first cough in every recording is likely to be a voluntary cough while the remaining coughs are more likely to be spontaneous.

For each cough recording, a Cough Property Vector is generated from the Contours as described elsewhere. The Patient Class Information is used to construct a Patient Class Descriptor, and the Diagnostic Information is used to construct a Diagnostic Descriptor. These elements are collectively used to train an appropriate Cough Class Descriptor in the Cough Database. This process is repeated for each available cough recording in Training Mode.

Constructing the Patient Class Descriptor (Training Mode)

In Training Mode, the Cough Classification Algorithm accepts as input information that organizes patients into different classes that reflect differences and commonalities between the proper diagnoses of patients in those classes and the properties of their coughs. The Patient Class Information employed in training mode corresponds to Patient Information that will be solicited from patients and provided to the Algorithm in Classification Mode.

Examples of useful Patient Class Information includes patient age groupings (<2 years; 2 to 10 years; 10 to 20 years; 20 to 30 years; etc.); patient sex (male and female); and patient smoking history (never smoked, current smoker, . . . ).

The Patient Class Information accepted in Training Mode is created using methods known to persons of ordinary skill in the art of characterizing information sets. For instance, the ages of all the patients in one training class may be represented either by the mean age of patients in the class, plus the variance of those ages, or by the minimum and maximum ages in the class.

The actual Patient Class Descriptor may be constructed as a binary structure, an SQL record, an XML document, or many other formats that will occur to person of ordinary skill in the art.

Constructing the Diagnostic Descriptor (Training Mode)

In one pertinent aspect, this classification system is useful for predicting diagnostic information for patients of a particular class with coughs with particular properties. When used for this purpose, the system must be trained by associating Diagnostic Information (such as whether patients have a respiratory illness) with patient information and cough properties.

As used in this application, the term "Diagnostic Information" includes but is not limited to both diagnoses arrived at via medical laboratory procedures, and diagnostic assessments of a patient's medical condition that a physician, nurse, technician, or other healthcare professional might arrive at as the result of a clinical evaluation.

In one simple and useful form, this Diagnostic Information may consist of diagnostic codes from the International Classification of Diseases developed by the World Health Organization, commonly referred to as ICD9. In another implementation, Diagnostic Information may consist codes reflecting an evaluation that a patient does or does not have a severe cough-transmissible respiratory illness, or a severe cough-generating respiratory illness, and/or whether the patient's respiratory system is normal or disordered, or other such evaluation of a patient's respiratory status as will occur to persons of ordinary skill in the art.

The actual Diagnostic Descriptor may be constructed as a binary structure, an SQL record, an XML document, or many other formats that will occur to person of ordinary skill in the art.

Training the Cough Class Descriptor (Training Mode)

In one implementation, each CCD in the Cough Database is trained as shown in FIG. 7. If the Cough Database does not exist, an empty database is created and initialized.

Once the Cough Database exists, it will be scanned for a CCD with a Patient Class Descriptor that matches the current Patient Class Descriptor, and a Diagnostic Descriptor that matches the current Diagnostic Descriptor. If no such CCD exists, a new CCD is created, and populated with the current Patient Class and Diagnostic Descriptors, and with an initialized null Cough Properties Descriptor.

Once the CCD that matches the current training data has been found or created, its Cough Properties Descriptor is "trained on" (that is, updated to reflect) the current Cough Property Vector, using update techniques appropriate for the implementation of the Cough Properties Descriptor in use, these techniques being well known to those of ordinary skill in the art. For example, if the Cough Properties Descriptor is a list of all of the Cough Property Vectors in the training set with comparable Patient and Diagnostic Information, the current Cough Property Vector is added to the list in the selected Cough Properties Descriptor. Alternatively, if the Cough Properties Descriptor is an estimated multidimensional Gaussian random variable, the current Cough Property Vector is used to update that estimate.

Constructing the Cough Class Candidate List (Classification Mode)

In Classification Mode, the operation of the Cough Classification Algorithm is to construct Cough Class Candidate List from the Cough Database. The Cough Classes in this list are the Cough Classes that an unknown cough most closely resembles, given that the Patient Information for the source of the unknown cough is comparable with the Patient Classes of those Candidates. The Cough Algorithm may further analyze the Diagnostic Information in the Candidate CCDs to predict a patient diagnosis, such as the likelihood that the patient has a severe cough-transmissible respiratory illness.

In one implementation, this operation proceeds as follows.

The recording of the patient's cough is preprocessed as described above. Coughness, Local Cough Property, and Cumulative Cough Property Contours are generated from the preprocessed audio signal. As described above, in one implementation, an optional configuration flag may specify that the first cough of every recording is to be ignored. An Utterance Cough Property Vector for the cough being classified is generated from the Contours.

The current Patient Information is used to select all CCDs in the Cough Database with comparable Patient Class Descriptors, using techniques that would be obvious to a person of ordinary skill in the art. For instance, in one implementation, each of the CCDs in the database is scanned, and its Patient Class Descriptor accessed. That Patient Class Descriptor is compared with the current Patient Information. If the current Patient Information is comparable with the current CCD, a link to that CCD is added to the Candidate List. In one implementation, if the sex of the current patient matches the sex of the Patient Class being examined, and the age of the current patient matches the age range of the Patient Class being examined, and the smoking history of the current patient matches the smoking history of the Patient Class being examined, the Patient Class is deemed comparable to the Patient Information, and the CCD being examined is added to the Cough Class Candidate List.

The set of selected CCDs form the Cough Class Candidates for the current cough. As shown in FIG. 8, each Candidate in the Cough Class Candidate List comprises a link to the Candidate's CCD and a Candidate Confidence Score. The Candidate Confidence Score reflects the confidence, or likelihood, that the current Utterance Cough Properties Vector is a similar to, or in the same class as, the Cough Property Vectors of the coughs the Cough Class was trained on. This Confidence Score can be calculated using any of several techniques known to persons of ordinary skill in the art. For instance, if the Cough Properties Descriptor takes the form of a multidimensional Gaussian estimate, as described above, a Single-Sample z Score can appropriately be used as a Candidate Confidence Score. If the Cough Properties Descriptor takes the form of a list of all of the Cough Properties Vectors in the training samples for the Class, an N Nearest Neighbor list can be constructed for the Utterance Cough Properties Vector as the Cough Database is being scanned, and the Confidence Score for a particular Cough Class can be calculated as the fraction of the N Nearest Neighbor list that corresponds to that Cough Class.

Predicting the Patient Diagnosis (Classification Mode)

In certain implementation of the Cough Classification Algorithm, when that Algorithm is operating in Classification Mode, and has constructed a Cough Class Candidate List, it predicts a patient diagnosis. This Prediction is generated from the Cough Class Candidate List, by analyzing the Diagnosis Descriptors in the List, and taking into consideration the Confidence Scores of the corresponding CCDs. The result of this prediction is the generation of a patient diagnosis that is compatible with the diagnoses of the patients in the training data set with similar Patient Information and similar cough properties.

In certain implementations, the user of the Algorithm can provide Prediction Control Parameters that control the results of the prediction process in useful ways. In one implementation, these Predication Control Parameters may specify either the maximum desired False Positive error rate, or the maximum desired False Negative error rate (but not both).

In one implementation of the Algorithm, the Prediction is generated by considering each Candidate to be a mutually exclusive alternative possible prediction, the Predication Control Parameter to be the maximum desired False Positive error rate, and the Confidence Scores to be estimates that the diagnosis specified by each Candidate Diagnostic Descriptor is the correct diagnosis. In this implementation, if the most likely Candidate (the Candidate with the highest Score) has a Score greater than the Prediction Control Parameter, that Candidate's Diagnostic Descriptor is output as the Patient Diagnostic Prediction. Otherwise, a null value, indicating that no prediction can be generated, is output.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions. Likewise, the acoustic signal may be segmented with different amplitude and frequency criteria than those used here.

The techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

What is claimed is:

1. A method performed by at least one computer processor, the method comprising:
   (A) receiving first acoustic data representing at least one first cough of a first human subject using a standalone microphone not in contact with the first human subject's body;
   (B) identifying at least one first value of at least one first acoustic property of the first acoustic data, wherein the at least one first acoustic property comprises at least one of amplitude, temporal structure, and zero-crossing rate;
   (C) determining, based on the at least one first value of the at least one first acoustic property, whether the first acoustic data indicates that the first human subject has a severe cough-transmissible respiratory illness, comprising:
      (1) extracting, from the first acoustic data, a coughness contour that identifies at least one cough-like region in the first acoustic data;
      (2) extracting, from the first acoustic data, contours of local and cumulative properties that are relevant for classifying coughs based on the first acoustic data;
      (3) generating a single vector of acoustic data property values from the coughness contour and the contour other than the coughness contour; and
      (4) determining, based on the single vector, whether the first acoustic data indicates that the first human subject has a severe cough-transmissible respiratory illness.

2. The method of claim 1, wherein the at least one first cough consists of exactly one cough of the first human subject.

3. The method of claim 1, wherein the at least one first cough comprises a plurality of coughs of the first human subject.

4. The method of claim 1, wherein (C) comprises determining, based on the at least one first value of the at least one first acoustic property, that the first acoustic data indicates that the first human subject has a severe cough-generating respiratory illness.

5. The method of claim 1, wherein (C) comprises determining that the first acoustic data indicates that the first human subject has a severe respiratory illness, and wherein the method further comprises:
   (D) receiving second acoustic data representing at least one second cough of a second human subject;
   (E) identifying at least one second value of at least one second acoustic property of the second acoustic data;
   (F) determining, based on the at least one second value of the at least one second acoustic property, that the second acoustic data indicates that the second human subject does not have a severe respiratory illness.

6. The method of claim 1, further comprising:
   (D) before (C), determining, based on at least one second value of at least one second acoustic property, that the first acoustic data represents a cough of the first human subject.

7. The method of claim 6, further comprising:
   (E) receiving second acoustic data representing a sound generated by a second human subject;
   (F) determining, based on at least one third value of at least one third acoustic property of the second acoustic data, that the second acoustic data does not represent a cough of the second human subject.

8. The method of claim 1, wherein (C) further comprises:
   (C) (5) identifying, based on the at least one first value of the at least one first acoustic property, a type of the severe cough-transmissible respiratory illness.

9. The method of claim 8, wherein (C) (5) comprises determining whether the severe cough-transmissible respiratory illness is of a type that can propagate via epidemics.

10. The method of claim 1, wherein the at least one acoustic property comprises a landmark instance identifying a point in the first acoustic data that marks a discrete event.

11. The method of claim 10, wherein the landmark instance comprises an instance of a consonantal landmark.

12. The method of claim 10, wherein the landmark instance comprises an instance of a vocalic landmark.

13. The method of claim 10, wherein (C) comprises identifying, within the first acoustic data, an inspiration phase of a first cough in the at least one first cough, a compression phase of the first cough, and an expiration phase of the first cough.

14. A non-transitory computer-readable medium tangibly storing computer program instructions, wherein the computer program instructions are executable by at least one computer processor to perform a method, the method comprising:
   (A) receiving first acoustic data representing at least one first cough of a first human subject using a standalone microphone not in contact with the first human subject's body;
   (B) identifying at least one first value of at least one first acoustic property of the first acoustic data, wherein the at least one first acoustic property comprises at least one of amplitude, temporal structure, and zero-crossing rate;
   (C) determining, based on the at least one first value of the at least one first acoustic property, whether the first acoustic data indicates that the first human subject has a severe cough-transmissible respiratory illness, comprising:
      (1) extracting, from the first acoustic data, a coughness contour that identifies at least one cough-like region in the first acoustic data;
      (2) extracting, from the first acoustic data, contours of local and cumulative properties that are relevant for classifying coughs based on the first acoustic data;
      (3) generating a single vector of acoustic data property values from the coughness contour and the contour other than the coughness contour; and
      (4) determining, based on the single vector, whether the first acoustic data indicates that the first human subject has a severe cough-transmissible respiratory illness.

15. A method performed by at least one computer processor, the method comprising:
   (A) receiving first acoustic data representing at least one first cough of a first human subject using a standalone microphone not in contact with the first human subject's body;
   (B) identifying at least one first value of at least one first acoustic property of the first acoustic data, wherein the at least one first acoustic property comprises at least one of amplitude, temporal structure, and zero-crossing rate;
   (C) determining, based on the at least one first value of the at least one first acoustic property, whether the first acoustic data indicates that the first human subject has an abnormal pulmonary system, comprising:

(1) extracting, from the first acoustic data, a coughness contour that identifies at least one cough-like region in the first acoustic data;
(2) extracting, from the first acoustic data, contours of local and cumulative properties that are relevant for classifying coughs based on the first acoustic data;
(3) generating a single vector of acoustic data property values from the coughness contour and the contour other than the coughness contour; and
(4) determining, based on the single vector, whether the first acoustic data indicates that the first human subject has an abnormal pulmonary system; and
(D) if the first acoustic data is determined to indicate that the first human subject has an abnormal pulmonary system, then determining, based on the at least one first value of the at least one first acoustic property, whether the first acoustic data indicates that the first human subject has a severe cough-transmissible respiratory illness.

16. The method of claim 15, wherein (C) comprises determining, based on the at least one first value of the at least one first acoustic property, that the first acoustic data indicates that the first human subject has a normal pulmonary system.

17. The method of claim 15, wherein the at least one first cough consists of exactly one cough of the first human subject.

18. The method of claim 15, wherein the at least one first cough comprises a plurality of coughs of the first human subject.

19. A non-transitory computer-readable medium tangibly storing computer program instructions, wherein the computer program instructions are executable by at least one computer processor to perform a method, the method comprising:
(A) receiving first acoustic data representing at least one first cough of a first human subject using a standalone microphone not in contact with the first human subject's body;
(B) identifying at least one first value of at least one first acoustic property of the first acoustic data, wherein the at least one first acoustic property comprises at least one of amplitude, temporal structure, and zero-crossing rate;
(C) determining, based on the at least one first value of the at least one first acoustic property, whether the first acoustic data indicates that the first human subject has an abnormal pulmonary system, comprising:
(1) extracting, from the first acoustic data, a coughness contour that identifies at least one cough-like region in the first acoustic data;
(2) extracting, from the first acoustic data, contours of local and cumulative properties that are relevant for classifying coughs based on the first acoustic data;
(3) generating a single vector of acoustic data property values from the coughness contour and the contour other than the coughness contour; and
(4) determining, based on the single vector, whether the first acoustic data indicates that the first human subject has an abnormal pulmonary system; and
(D) if the first acoustic data is determined to indicate that the first human subject has an abnormal pulmonary system, then determining, based on the at least one first value of the at least one first acoustic property, whether the first acoustic data indicates that the first human subject has a severe cough-transmissible respiratory illness.

20. The method of claim 1:
wherein the at least one first acoustic property includes temporal structure and zero-crossing,
wherein the at least one first value of the at least one first acoustic property includes a value of the temporal structure and a value of the zero-crossing; and
wherein determining comprises determining, based on the value of the temporal structure and the value of the zero-crossing, whether the first acoustic data indicates that the first human subject has a severe respiratory illness.

21. The method of claim 1:
wherein the at least one first acoustic property includes amplitude, temporal structure, and zero-crossing rate;
wherein the at least one first value of the at least one first acoustic property includes a value of the amplitude, a value of the temporal structure, and a value of the zero-crossing rate; and
wherein determining comprises determining, based on the value of the amplitude, the value of the temporal structure, and the value of the zero-crossing rate, whether the first acoustic data indicates that the first human subject has a severe respiratory illness.

22. The method of claim 21, wherein the at least one first cough includes a first cough and a second cough; and
wherein (C) comprises determining whether the first cough and the second cough are separated from each other by at least 50 ms.

23. The method of claim 1, wherein (C) comprises determining whether the onset of the at least one first cough includes a rise of at least 15 dB in at most 12 ms.

24. The method of claim 1, wherein (C) comprises determining whether the onset of the at least one first cough to its maximum is at least 15 ms.

25. The method of claim 1, wherein all broad frequency ranges within 1-7 kHz in the first acoustic data rise and fall together.

26. The method of claim 1, wherein the difference between the maximum over frequency and the median over frequency in the first acoustic data lies in the range 30-45 dB.

27. The method of claim 1, wherein, at each time during the first acoustic data, the standard deviation over frequency is at least 3.5 dB.

28. The method of claim 1, wherein (C) comprises determining whether one-half of the zero-crossing rate is at least 2 kHz for at least 20 ms.

* * * * *